United States Patent [19]  [11] Patent Number: 4,925,985
Williams et al.  [45] Date of Patent: May 15, 1990

[54] PROCESS FOR THE PRODUCTION OF 4,6-DIMETHYL-7-HYDROXYNONAN-3-ONE

[75] Inventors: David L. Williams; William B. Edwards, III, both of Richmond; Richard H. Cox; Daryl L. Faustini, both of Midlothian; Surnease Drew, Richmond, all of Va.

[73] Assignee: Philip Morris Incorporated, New York, N.Y.

[21] Appl. No.: 266,162

[22] Filed: Nov. 2, 1988

[51] Int. Cl.$^5$ .............................................. C07C 45/67
[52] U.S. Cl. ..................................... 568/384; 568/386; 568/392; 568/404; 560/266; 558/435; 558/440; 549/356
[58] Field of Search ............... 568/386, 384, 392, 404; 560/266; 558/435, 440; 549/356

[56] References Cited
U.S. PATENT DOCUMENTS 4,317,836 3/1982 Chuman et al. .................... 568/414

OTHER PUBLICATIONS

Ono et al., Agric. Biol. chem., vol. 44, pp. 2259–2260 (1980).
Chuman et al., Agric. Biol. Chem., vol. 46, pp. 593–595 & 3109–12 (1982).
Mochiguki et al., Agric. Biol. Chem., vol. 48, pp. 2833–2834 (1984).
Mori et al., J. chem. Ecology, vol. 12, pp. 83–89 (1980).
Levinson et al., Naturwissenschaften, #73, S36(1986).
Chuman et al., J. Chem., Ecology, vol. 11, #4 (1985).

Primary Examiner—James H. Reamer

[57] ABSTRACT

A process for the production of 4,6-dimethyl-7-hydroxynonan-3-one of specific stereochemistry is disclosed. The process results in an active (+)-serricornin.

4 Claims, 7 Drawing Sheets

4,6-Dimethyl-7-hydroxy-3-nonanone

Natural Pheromone 6,7-"Threo"-Diastereomers 6,7-"Erythro"-Diastereomers

Fig. 4
2,6-Diethyl-3,5-dimethyl-2-hydroxy-4H-2,3,5,6-tetrahydropyran

2,4-DIMETHYL-5-OXOHEPTANITRILE

Fig. 9
PILOT STUDY TRAP COUNTS 1. (±)-Serricornin IVd from IVc
2. Fuji Flavor Co. Ltd. Pheromone

PROCESS FOR THE PRODUCTION OF 4,6-DIMETHYL-7-HYDROXYNONAN-3-ONE

BACKGROUND OF THE INVENTION

This invention relates to an improved method for the production of 4,6-dimethyl-7-hydroxynonan-3-one.

The female cigarette beetle (Lasioderma Serricorne F.) has been shown to secrete a sex pheromone which attracts the male beetle. This pheromone has been identified in the literature as (4S,6S,7S)-4,6-dimethyl-7-hydroxynonan-3-one.

The sex pheromone may be applied to pest prevention by attracting male insects to a given place to catch and kill them or by disturbing the normal mating behavior of male cigarette beetles. Alternatively, a sex pheromone may be used to attract and collect insect pests in order to make a field survey on the hatching or growing of the insect pests. On the basis of the results of such periodic surveys, it is possible to judge whether insecticide spraying is needed or not and to select the effective amount of an insecticide, thereby reducing the quantity of the insecticide used as a whole.

Research has been made on pest prevention by attracting insects for catching and killing them, or disturbing the communication between male and female insects using an insect sex pheromone.

In general, the paring behavior of insects is controlled by an extremely small amount of an odorous substance secreted by the insect, usually the female insect. The female insect releases a volatile, odorous substance in the air. The male insect perceives this odor and moves on legs or wings toward the female insect who is the source of the odor. The male insect who finds the female insect, sexually excites and mates therewith.

One type of odorous substance secreted by female insects is generally called a sex pheromone or sex attractant and is a very important substance in the mating behavior of insects.

DESCRIPTION OF THE PRIOR ART

The use of 4,6 dimethyl-7-hydroxynonan-3-one as a sex attracting composition is known in the art and it is the subject matter of U.S. Pat. No. 4,317,836. The patentees disclose both a pure compound and the use of the same as a sex attractant in the prevention of the cigarette beetle (lasioderma serricornin F.) which is an insect pest feeding on cured tobacco leaves and which causes serious damage to the tobacco industry. The serricornin of U.S. Pat. No. 4,317,836 is isolated from a natural product.

The literature also discloses a wide variety of techniques for the actual synthesis of (±)-serricornin (as opposed to its isolation) and a substantial number of the syntheses have as a key intermediate the production of 5-hydroxy-2,4-dimethylheptanenitrile (see for example Ono et al, *Agriculture Biological Chemistry*, volume 44 (number 9) pages 2259–2260 (1980) as well as Canadian patent 1,160,240. The production of (±)-serricornin from said intermediate compound is a synthesis well known in the art and the disclosure of the Ono et al article and said Canadian patent being herein incorporated by reference.

DESCRIPTION OF THE PREFERRED EMBODIMENTS

It is known in the art that 4,6-dimethyl-7-hydroxynonan-3-one is in reality a mixture of optical isomers. Thus, the natural pheromone is one of eight optical isomers which are possible for serricornin due to its three asymmetric carbon atoms (C-4, C-6 and C-7). More recently, it has been shown that each of these optical isomers can exist in two different forms—open or cyclic. Consequently there are 24 possible isomers of 4,6-dimethyl-7-hydroxy-nonan-3-one.

The isomers have been studied in great detail in the literature and it has been reported that the ratio of 6,7-threo to 6,7-erythro for (±)-serricornin is of importance in determining the effectiveness of the compound for the attraction of male cigarette beetles. Thus, it has been reported in the literature that the 6,7-threo isomers were at least a thousand times more active than 6,7-erythro isomers. While obviously the 6,7 threo to 6,7-erythro isomer ratio is of extreme importance in producing an effective compound in producing an effective cigarette beetle attraction, it is not the sole determinant factor. Trace amounts of impurities, as well as synergistic/antagonistic effects of various isomers can have a disastrous effect on activity.

Literature articles discussing the importance of the ratios include: Chuman et al, *Agriculture Biological Chemistry*, Volume 46 (No. 2) pages 593-595 (1982), Chuman et al, *Agriculture Biological Chemistry*, Volume 46 (No. 12), pages 3109-3112 (1982), Mochizuki et al, *Agriculture Biological Chemistry*, Volume 48, (No. 11), pages 2833-2834 1984), Mori et al, *Journal of Chemical Ecology*, Volume 12, (No. 1), pages 83–89 (1986)and Levinson et al, *Naturwissenschaften* 73, S. 36 (1986), the disclosure of said articles being herein incorporated by reference.

The novel process of this invention is predicted on the discovery that the stereochemistry of the (±)-serricornin is set at the production of 5-hydroxy-2,4-dimethylheptanitrile and once the stereochemistry of this intermediate compound is set the processing of this intermediate to the final product does not seriously affect the final 6,7-threo/erythro isomer ratio.

However, as will be demonstrated later, the setting of the ratio is but one factor in determining the activity of the final product. Very specific purification techniques are required and unless the purification techniques are carried out, optimum activity will not be obtained even though the isomer ratio has been set.

DETAILED DESCRIPTION OF THE INVENTION

The novel process of this invention involves a series of process steps which are mutually essential to produce the (±)-serricornin having enhanced activity.

The manufacture of (±)-serricornin (Compound IVd of FIG. 2) is carried out by reacting pyrrolidine and 3-pentanone in the presence of p-toluenesulfonic acid monohydrate in order to obtain N-(1-ethyl-1-propenyl)-pyrrolidine. This compound is shown as I in FIG. 1 and its method of preparation is a standard procedure which is reported in the literature. No novelty is claimed for this step. In step 2, compound I is reacted with methacrylonitrile in absolute alcohol in order to produce 2-4-dimethyl-5-oxoheptanitrile which is identified as IIa in FIG. 1. This reaction is also old in the literature and no novelty is claimed for this step.

Figure 1:
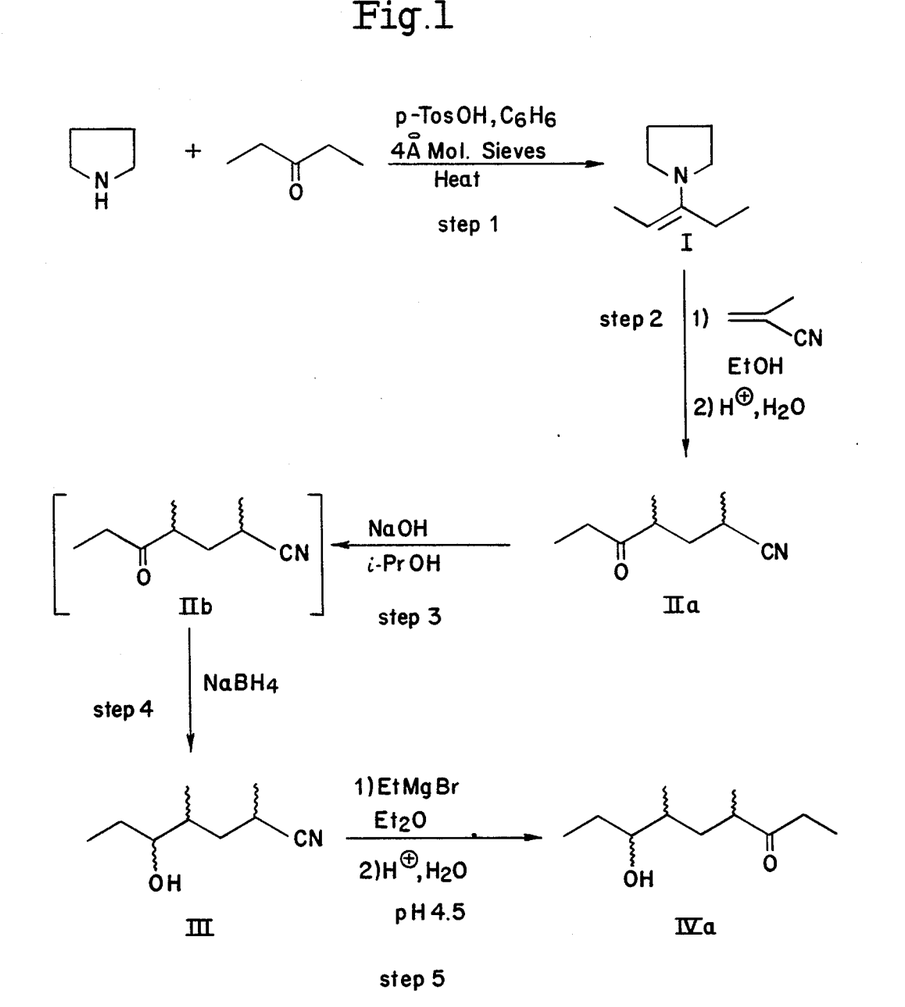
FIG. 1 represents in schematic form the synthesis of the 4,6-dimethyl-7-hydroxynonan-3-one in an unpurified form.
Figure 8:
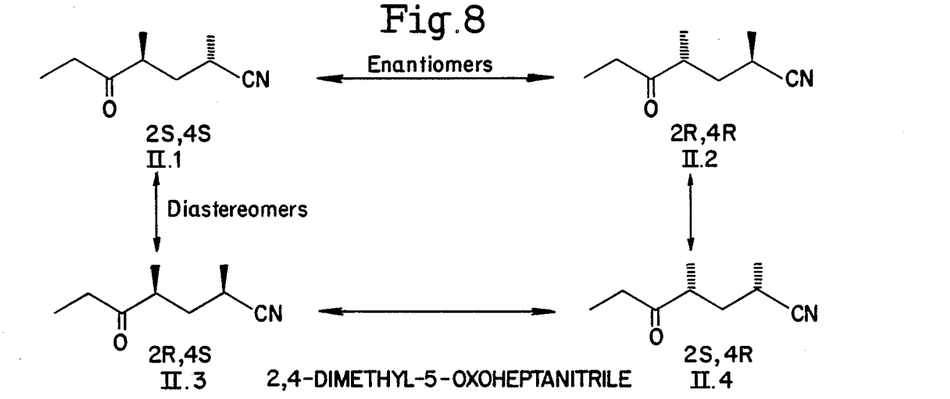
FIG. 8 depicts the 4 isomers of 2,4-dimethyl-5-oxoheptanitrile.

The novel approach of this invention really begins in the treatment of IIa in order to produce a product which is identified as IIb in FIG. 1. This is fundamentally a base equilibration of IIa to give IIb with a reproducible ratio of stereoisomers. The importance of the base equilibration step can be best explained by reference to certain of the figures. Compound IIa of FIG. 1 has two asymmetric carbon atoms namely C-2 and C-4. As such it can exist in four different isomeric forms. These four isomeric forms are set forth in FIG. 8. As prepared by the prior art, including the reaction scheme set forth in FIG. 1, this compound is a mixture of two racemic compounds, i.e., it is a mixture of all 4 isomers depicted in FIG. 8 with the amount of II.1 equaling II.2 and II.3 equaling II.4 because these are enantiomers. The ratio of II.1 to II.3 and consequently II.2 to II.4 can vary depending on the method of synthesis of IIa.

Investigation has shown that the ratio of diastereomers can change from reaction to reaction using the very same synthesis for IIa and during the purification of the product by conventional means such as vacuum distillation. The novel process of this invention consistently gave the same ratio of isomers regardless of the starting ratio. Thus, even when a base equilibration is run on IIa which is approximately 95 +% of one diastereomer or the other, the final product has the same diastereomer ratio. Thus, the base equilibration of IIa gives the thermodynamic product.

In order to ensure that it is the thermodynamic product which is reduced in step 4 of FIG. 1, the equilibrated product IIb of FIG. 1 is not isolated but is reduced by direct treatment of the product solution from step 3 with sodium borohydride.

Figure 3:
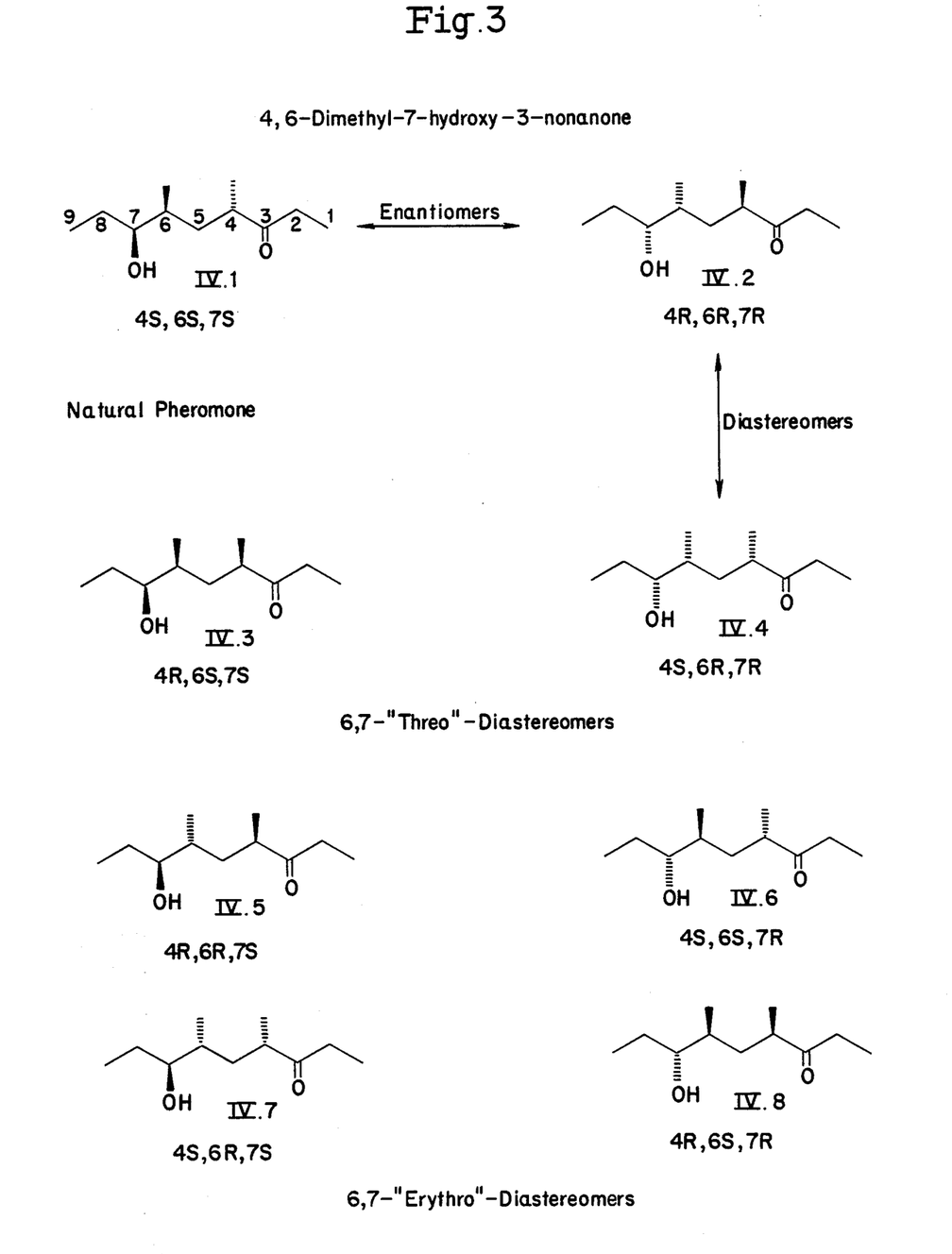
FIG. 3 depicts the 8 optical isomers of serricornin.
Figure 4:
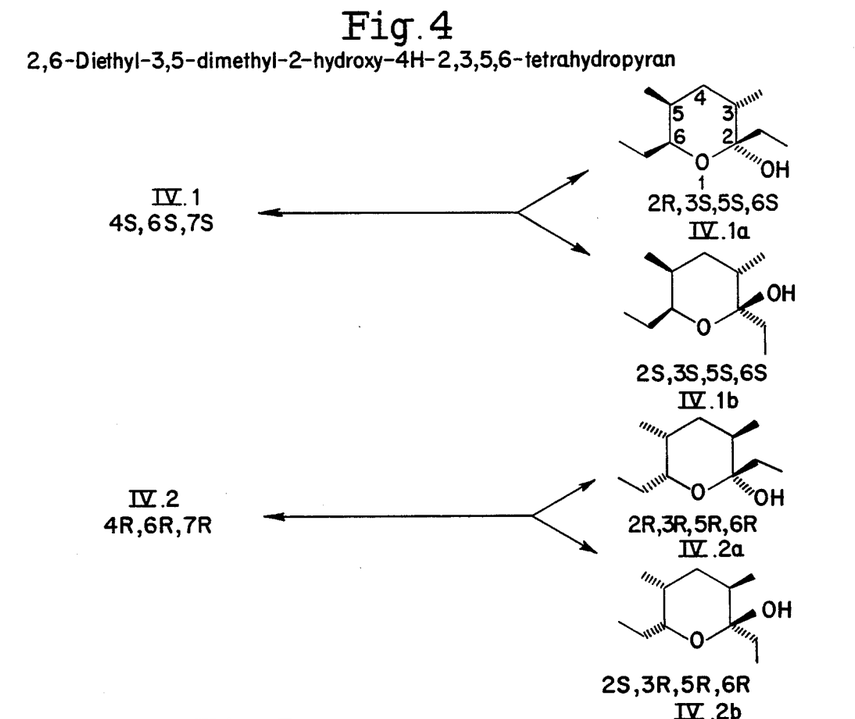
FIGS. 4, 5 and 6, and 7 depict the fact that each optical isomer of FIG. 3 can exist in two additional forms, open and cyclic.
Figure 5:
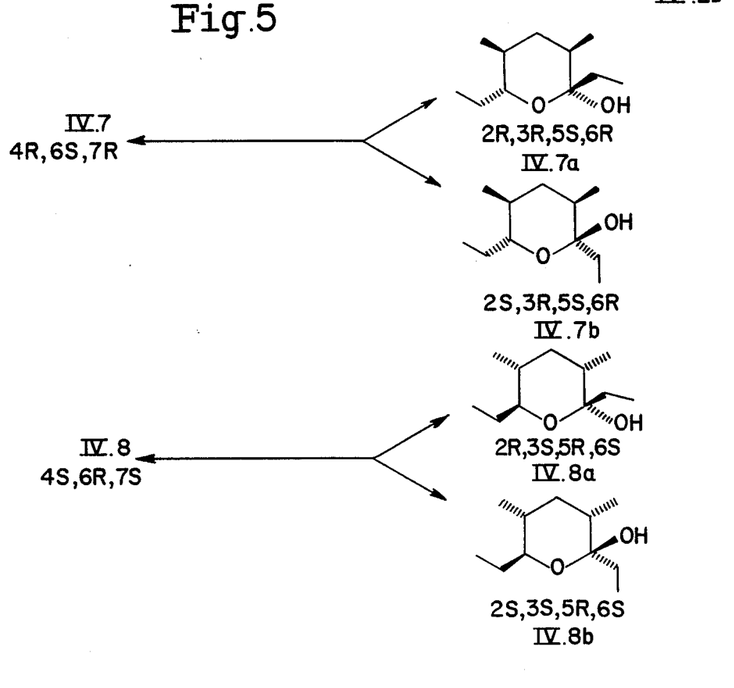
Figure 6:
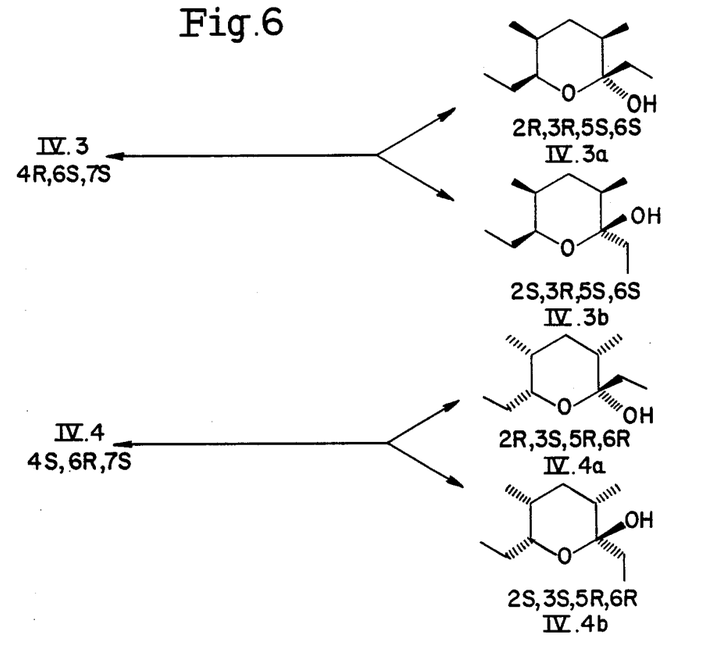

As has heretofore been set forth, the consequences of this equilibration are that the stereochemistry at C-2 and C-4 of IIb are reproducibly fixed prior to the final reduction step. The stereochemistry of these carbon atoms affect the reduction carried out in step 4 of FIG. 1, i.e., a different isomer ratio for IIb would be reduced to give III with a different isomer ratio. Once the stereochemistry at C-4 and C-5 of III are set they stay unaltered throughout the remainder of the synthesis. Therefore, the setting of the IIb isomer ratio is the determining factor in setting the stereochemistry at C-4 and C-5 for III, and it defines the stereochemistry of C-6 and C-7 of (±)-serricornin, i.e., the 6,7-threo/erythro isomer ratio (see FIG. 3).

The base equilibration can be carried out by treatment of IIa with a suitable base such as sodium hydroxide, lithium hydroxide, calcium hydroxide, etc. The reaction is carried out at temperatures ranging from −20° C. to 40° C., conveniently at atmospheric pressure, for a period of time ranging from 2 to 48 hours.

The reduction of the ketone to produce 2,4-dimethyl-5-hydroxyheptanenitrile is also a very critical step. It involves the reduction of the ketone with a conventional reducing agent such as sodium borohydride but in the presence of added base. It is to be understood that the sodium borohydride reduction of a ketone functional group is a standard, well established procedure and it is known in the art that sodium borohydride reduces IIA of FIG. 1 to III of FIG. 1. See the Levinson et al and the Ono et al publications previously mentioned. The reaction conditions of this invention are similar to those used by Ono et al with two critical differences. In the process of the instant invention, the reaction is run on the equilibrated material (IIb) and, equally important, the reaction is run in presence of a base. The full consequences of the added base in carrying out this reaction are not completely understood but without it inferior results are obtained with regard to the effectiveness of the desired final product.

The bases which are applicable to this step are the same as those applicable in the prior step. The reaction is usually carried out in a solvent such as aliphatic alcohols or water. It is preferred to use isopropanol.

The next step in the novel process of this invention involves the reaction of 2,4-dimethyl-5-hydroxyheptanenitrile (Compound III of FIG. 1) with a Grignard reagent such as ethyl magnesium bromide to obtain the crude (±)-serricornin (IVa in FIG. 1). The reaction conditions employed are essentially identical to those reported in the literature, i.e., Levinson et al and Ono et al, previously referred to. The crude (±)-serricornin, i.e., Compound IVa of FIG. 1, is then purified by either of two separate and distinct routes which are labeled as A and B in FIG. 2. Briefly put, procedure A involves converting the (±)-serricornin, i.e., Compound IVA from FIG. 2, via dehydration to (±) anhydroserricornin, i.e., Compound V in FIG. 2, followed by rehydration of (±)-anhydroserricornin (V of FIG. 2) to (±)-serricornin, (IVC of FIG. 2) from which trace impurities have been removed, i.e., but needs to be equilibrated at the 4 carbon atom to obtain a stable/optimum mixture of isomers.

Figure 2:
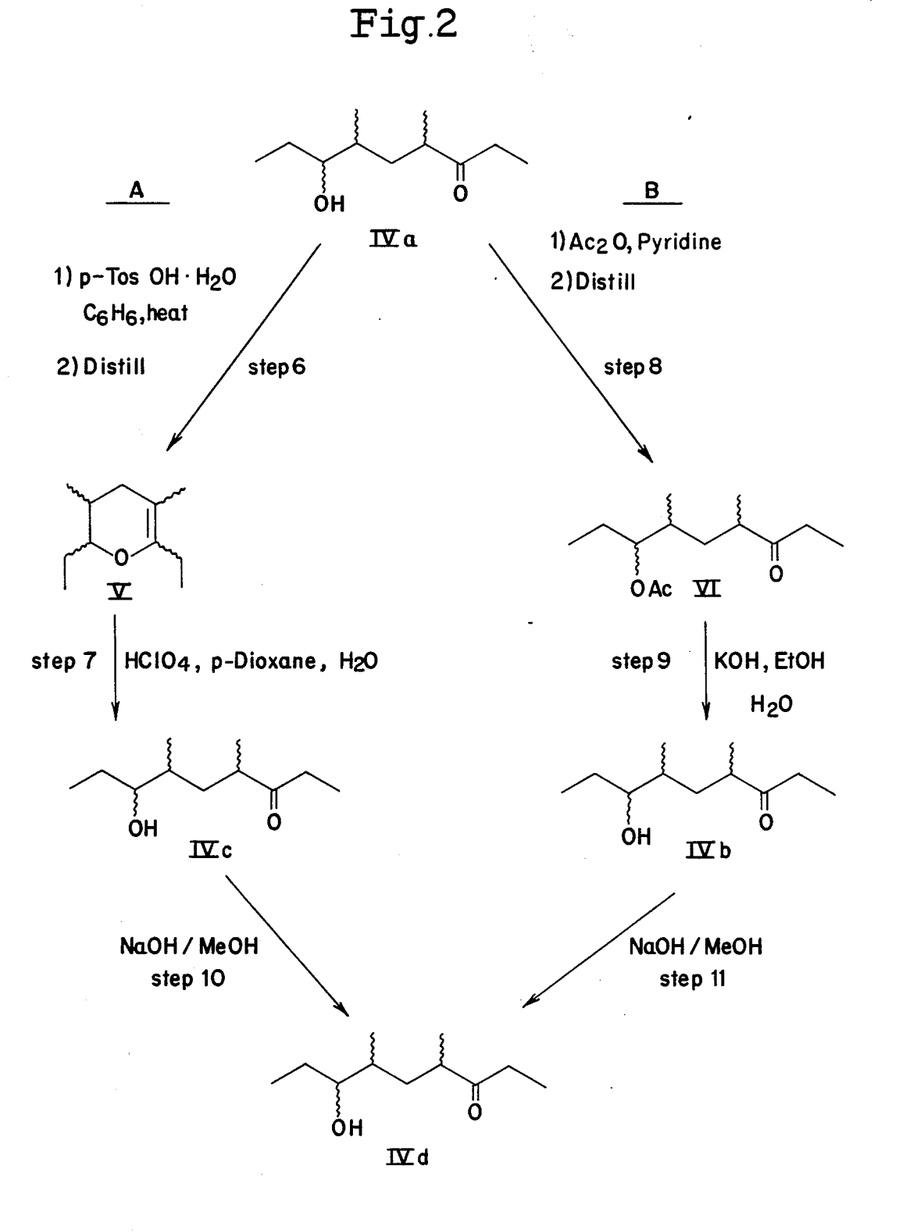
FIG. 2 represents, in schematic form, two separate purification techniques identified as A and B, either of which must be used in order to produce 4,6-dimethyl-7-hydroxynonan-3-one of enhanced activity.

The purification procedure identified as B in FIG. 2 can briefly be described as the acylation of (±)-serricornin, i.e., Compound IVA, in order to obtain 4,6-dimethyl-7-acetoxynonan-3-one (Compound VI of FIG. 2), followed by conversion of the Compound VI of FIG. 2 to (±)-serricornin (Compound IVB of FIG. 2) from which trace impurities have been removed, i.e., but needs to be equilibrated at the 4 carbon atom to obtain a stable/optimum mixture of isomers.

Although both procedure A and procedure B utilize different methods, nevertheless they both start with an impure (±)-serricornin, i.e., IVA, and they involve the production of a purified (±) serricornin, i.e., IVC of FIG. 2 for procedure A and IVB of FIG. 2 for procedure B.

In order to complete the purification process from either procedure A or procedure B, both products must be subject to a base equilibration step which involves contacting the material dissolved in a suitable solvent such as alcohol with an appropriate base. The nature of the base is not narrowly critical but it is preferred to use sodium hydroxide. This serves to optimize and equilibrate the compound at the 4 carbon.

As will be illustrated in the examples which follow, the novel process of this invention, including the purification procedures, involves a series of steps which interconnect in some way to produce a material having enhanced activity.

The following examples will now illustrate the novel process of this invention.

EXAMPLE 1

Synthesis of N-(1-ethyl-1-propenyl) pyrrolidine (Compound I, FIG. 1)

Pyrrolidine (1608 g, 22.6 moles), 3-pentanone (860 g, 9.98 moles), and p-toluenesulfonic acid monohydrate (470mg, 2.7 moles) were placed in dry benzene (5.4L) in a 12 liter 3-neck round bottom flask equipped with a soxlet extractor containing 4A molecular sieves (2Kg). The solution was refluxed for 20 hours under a nitrogen atmosphere. The reaction mixture was then cooled and the solvent removed under reduced pressure (30 mm). The resulting crude enamine was distilled at 38–40° C. and 0.70 mm to give a 75.5% yield of I (1048 g, 7.54 moles). GC and NMR data confirmed the above structure.

The reaction was repeated on the same molar scale and a yield of 85% of I was obtained.

EXAMPLE 2

Synthesis of 2.4-Dimethyl-5-Oxoheptanenitrile (Compound IIa, FIG. 1)

The enamine (I, 1182 g, 8.50 moles) and methacrylonitrile (581 g, 8.67 moles) were combined in absolute ethanol (6.8L) in a 12 liter round bottom flask. The stirring mixture was then refluxed for 18 hours under nitrogen. The mixture was cooled and the ethanol removed under reduced pressure (30 mm). Diethyl ether (1L) and water (1L) were added to the residue. After shaking in a separatory funnel, the organic layer was removed and the aqueous layer again extracted with diethyl ether (1L). The combined organic layers were washed with 10% aqueous hydrochloric acid (2×500 ml) and with saturated aqueous sodium chloride solution (500 ml). After drying (MgSO$_4$), the solvent was removed and the crude produced distilled at 61°–64° C. and 0.20 mm to give a 60% yield of 2,4-dimethyl-5-oxoheptanenitrile (799 g, 5.22 moles). IR, NMR, and MS data confirmed the above structure.

EXAMPLE 3

Equilibration to 2,4-Dimethyl-5-Oxoheptanenitrile (Compound IIb)

To a stirred solution of 2,4-dimethyl-5-oxoheptanenitrile (IIa 957 g, 6.25 moles) in isopropyl alcohol (5L) under a nitrogen atmosphere was added a catalytic amount of 50% aqueous sodium hydroxide (20 drops, ~400mg). This solution was stirred for 20 hours at room temperature. The alcoholic solution of IIb may be carried directly to the next step.

As has heretofore been pointed out, this is one of the most crucial steps in the novel process of this invention and the importance of this step can be best illustrated with reference to the following table which sets forth various diastereomer ratios for compounds IIa and IIb of FIG. 1. In the table which follows, seven separate runs were carried out and the diasteronic ratio for IIa and IIb were determined both in the crude form prior to purification i.e., see Example 2; the distilled form i.e., the product from Example 2 (after distillation); IIa which is purified by high performance liquid chromatography to obtain each diastereomer; and, finally, IIb from example III. The results are shown in Table 1.

TABLE 1

| | Diastereomer Ratios for IIa and IIb Isomer Ratios[1,2] | | | |
|---|---|---|---|---|
| Run | Crude IIa[3] | Distilled IIa[4] | IIa Isomer[5] | IIb[6] |
| 1 | 59.9/40.1 | 55/45 | NA[7] | ND[8] |
| 2 | ND | 52.6/47.4 | NA | ND |
| 3 | NA | NA | 98/2 | 67.5/32.5 |
| 4 | NA | NA | 5/95 | 67.7/32.3 |
| 5 | ND | 68/32 | NA | 65/35 |
| 6 | ND | 57.5/42.5 | NA | 63/37 |
| 7 | 62.3/37.7 | 61.5/38.5 | NA | ND |

Figure 7:
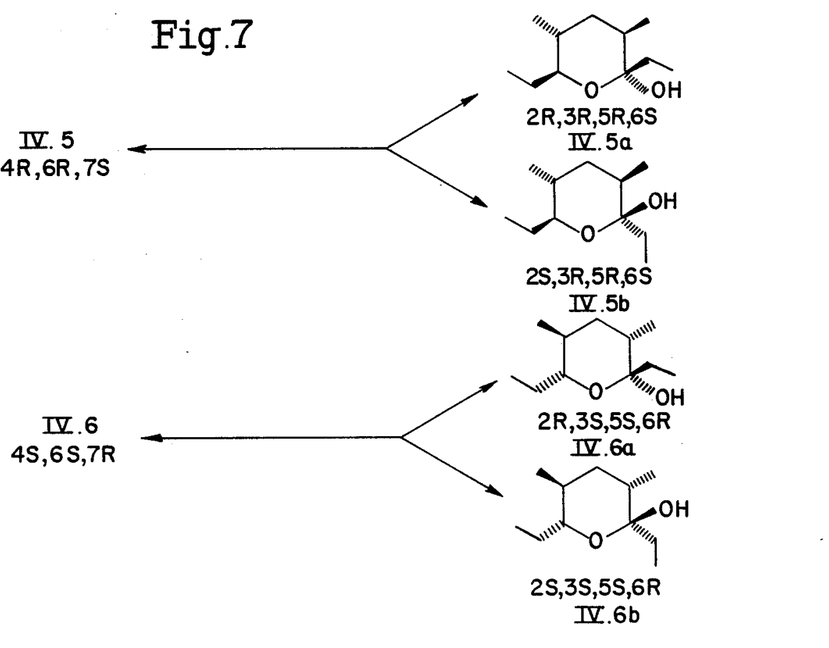

[1]Ratio is IIb.1/IIb.2:IIb.3/IIb.4 (FIG. 7)
[2]Determined by gas chromatography
[3]IIa from step 2 prior to purification
[4]Product (IIa) from step 2
[5]IIa purified by high performance liquid chromatography to obtain each diastereomer
[6]Product (IIb) from step 3
[7]Not applicable
[8]Not determined As can be seen from Table 1, the base catalyzed equilibration, i.e., IIb, is always approximately the same irrespective of the ratio of isomers which existed before this step. Compare runs 3, 4, 5 and 6 and it can been seen the base equilibration step produced a product which had a fairly uniform ratio of isomers.

EXAMPLE 4

Synthesis of 2,4-Dimethyl-5-Hydroxyheptanenitrile (Compound III, FIG. 1)

To a stirred solution of 2,4-dimethyl-5-oxoheptanenitrile (IIb, 239 g, 1.56 moles) in isopropanol (2.5L) at 5° C. under a nitrogen atmosphere, was added sodium borohydride (60 g, 1.59 moles) over a 15 minute period. The mixture was stirred for 40 hours at room temperature, after which GC analysis indicated complete reaction. The reaction mixture was cooled to −5° C. and carefully quenched with water (1L) followed by saturated aqueous ammonium chloride (200 ml). After the gas evolution had subsided, the isopropanol was removed under reduced pressure (30 mm). The residue was extracted with diethyl ether (1×750 ml, 2×350 ml) and the combined organic layers washed with water (2×200 ml) and saturated aqueous sodium chloride (200 ml). After drying (MgSO$_4$), the solvent was removed at reduced pressure (30 mm) and the crude product distilled at 75–80° C. and 0.20–0.10 mm to give a 88% yield of 2,4-dimethyl-5-hydroxyheptanenitrile (212 g, 1.37 moles).

IR, NMR, and MS data confirmed the above structure.

EXAMPLE 5

Synthesis of 4,6-Dimethyl-7-hydroxynonan-3-one (±)-Serricornin (Compound IVa, FIG. 1)

A solution of 2,4-dimethyl-5-hydroxyheptanenitrile (III, 25 g, 0.16 mole) in anhydrous diethyl ether (700ml) was set stirring with a mechanical stirrer under a nitrogen atmosphere. After cooling the solution to −10° C., 2.8 molar ethylmagnesium bromide (127 ml in hexane, 0.36 mole) was added dropwise over 20 minutes. A thick white precipitate formed which was stirred for 18 hours at room temperature.

The reaction mixture was cooled to −0° C. and carefully quenched with water (100 ml), followed by saturated aqueous ammonium chloride (75 ml). After stirring for 15 minutes, a buffer mixture of sodium acetate (41 g)/acetic acid (87 ml)/water (87 ml) was added over 20 minutes. The pH of the reaction mixture was then adjusted to pH 4.5 with careful addition of 6N hydrochloric acid and stirred for 1 hour at room temperature. The ethereal layer was removed and the aqueous layer extracted with diethyl ether (2×350 ml). The combined organic layers were washed successively with water (200 ml), saturated aqueous sodium bicarbonate (3×200 ml), water (200 ml) and a saturated aqueous solution of sodium chloride (200 ml). After drying ($MgSO_4$), the solvent was removed to give a 83% yield of (±)-serricornin (25 g, 0.13 mole).

It is to be understood that prior to use the above compound must be purified since at this stage its activity is obviously not as great as the purified product. Methods of purification of (±)-serricornin are well known in the art and are mentioned in the articles previously referred to.

Examples 6, 7 and 8 illustrate the purification scheme identified as A in FIG. 2.

EXAMPLE 6

Synthesis of 4,6-diethyl-3,5-dimethyl-2H-pyran, anhydroserricorni (Compound V, FIG. 2)

Compound IVa (18 g, 0.097 mole) was dissolved in benzene (180 ml) containing a catalytic amount (0.01 mole equivalents) of p-toluenesulfonic acid monohydrate. The stirring solution was refluxed under nitrogen for 18 hours using a Dean-Stark trap system to collect the water. The reaction mixture was cooled and 75% of the benzene was removed under reduced pressure (30 mm). The mixture was quickly filtered under a nitrogen atmosphere to remove any residues. The crude product was distilled at 87°–90° C. and 30 mm to give a 80% yield of pure anhydroserricornin (13 g, 0.077 mole).

It is to be understood that this particular method of dehydration is not novel per se and is, in fact, disclosed by Chuman et al, *Journal of Chemical Ecology*, Vol. 11, No. 4 (1985), the entire disclosure of which is incorporated herein by reference.

EXAMPLE 7

Synthesis of 4,6-Dimethyl-7-hydroxynonan-3-one, (±)-Serricornin (Compound IVc, FIG. 2)

Freshly distilled anhydroserricornin (V, 13 g, 0.077 mole) was set stirring in peroxide-free dioxane (690 ml passed through basic alumina, Activity 1) under a nitrogen atmosphere. Water (120 ml) and 0.01 N perchloric acid (120 mg in 120 ml water, 1.2 mmoles) were added and the resulting solution was stirred at room temperature for 18 hours. The solution was then neutralized with aqueous sodium bicarbonate to pH7 and most of the dioxane was removed under reduced pressure (30 mm). Water (100 ml) was added and the resulting mixture extracted with diethyl ether (1×400 ml, 2×200 ml). The combined organic layers were washed with water (100 ml) and then with saturated aqueous sodium chloride (100 ml). The ether solution was dried ($MgSO_4$) and solvent removed to give a 90% yield of purified (±)-serricornin (13 g, 0.070 mole).

The above rehydration of (±)-anhydroserricornin is quite different than the one described in the Chuman et al reference mentioned in connection with Example 6. It has been found that if conditions other than those set forth in Example 7 are used to rehydrate Compound V, the resulting (±)-serricornin will contain impurities which lower its pheromone activity.

A principal contaminant resulting from inappropriate rehydration conditions is (±)-anhydroserricornin (V, FIG. 2). The procedure of Example 7 rehydrates V in dioxane and water using perchloric acid as the catalyst. The product (IVc) is obtained in an average yield of 90% and is free of all (±)-anhydroserricornin and is essentially 100% pure.

EXAMPLE 8

Equilibration to 4,6-Dimethyl-7-hydroxynonan-3-one, (±)-serricornin (Compound IVd, FIG. 2)

Compound IVc (3.08 g, 0.017 mole) was dissolved in methanol (140 ml) and sodium hydroxide (64 mg, 1.6 mmole) was added to this stirring solution under a nitrogen atmosphere. The solution was then stirred for 72 hours at room temperature. Approximately 75% of the methanol was removed under reduced pressure (30 mm) after which diethyl ether (70 ml) and water (40 ml) were added. The ethereal layer was removed and the aqueous phase extracted with diethyl ether (3×40 ml). The combined organic layers were washed with water (40 ml) and then with saturated aqueous sodium chloride (50 ml) and dried ($MgSO_4$). The solvent was removed to give a 97% recovery of (±)-serricornin (3.0 g, 0.016 mmol).

GLC, HPLC, TLC, IR, and MS confirmed the basic structure. NMR confirmed the cyclic and acyclic forms of equilibrated (±)-serricornin as well as the ratios of the diastereomers.

The final step in the purification, as represented by Example 8, is believed to be novel (step 10 of FIG. 2).

A threo/erythro ratio of 73/27 was found (Table 2).

TABLE 2

| (±)-Serricornin Isomer Ratios[1,2]-Purification Effects | | | | | |
|---|---|---|---|---|---|
| Product | Step | IV.1; IV.2 | IV.3; IV.4 | IV.5; IV.6 | IV.7; IV.8 | 6,7-Threo/Erythro Ratio |
| Example 1 | | | | | | |
| (±)-Serricornin (IVa) | 5 | 49.8 | 36.4 | 5.4 | 8.4 | 86.2/13.8 |
| (±)-Serricornin (IVc) | 7 | 35.4 | 42.3 | 7.3 | 14.9 | 77.7/23.3 |
| (±)-Serricornin (IVd) | 10 | 31.4 | 41.9 | 9.6 | 17.1 | 73.3/26.7 |
| Example 2 | | | | | | |
| (±)-Serricornin (IVa) | 5 | 53.5 | 31.1 | 6.2 | 9.2 | 84.6/15.4 |
| (±)-Serricornin (IVc) | 7 | 28.5 | 45.6 | 8.4 | 17.5 | 74.1/25.9 |
| (±)-Serricornin (IVd) | 10 | 33.7 | 42.8 | 9.0 | 15.5 | 76.5/23.5 |
| Example 3 | | | | | | |
| (±)-Serricornin (IVb) | 9 | 53.5 | 32.3 | trace | 14.2 | 85.8/14.2 |
| (±)-Serricornin (IVd) | 11 | 53.7 | 22.8 | 4.4 | 19.1 | 76.5/23.5 |
| Example 4 | | | | | | |
| (±)-Serricornin (IVb) | 9 | 52.3 | 20.5 | 9.4 | 17.8 | 72.8/27.2 |
| (±)-Serricornin (IVd) | 11 | 54.1 | 18.5 | 10.0 | 17.3 | 72.6/27.4 |

[1]Ratios determined by Nuclear Magnetic Resonance.
[2]Each of the isomers may exist partially or completely in its respective cyclic forms.

Examples 9–11 represent purification Scheme B set forth in FIG. 2.

EXAMPLE 9

Synthesis of 4,6-Dimethyl-7-acetoxynonan-3-one (Compound VI, FIG. 2)

A solution of 4,6-dimethyl-7-hydroxynonan-3-one (IVa, 10 g, 53.8 mmoles) in acetic anhydride (13.8 g, 135 mmoles) and pyridine (12.8 g, 162 mmoles) was set stirring under a nitrogen atmosphere. After stirring for 20 hours at room temperature, most of the acetic anhydride and pyridine were removed at reduced pressure to leave a clear oil (11 g crude weight). The crude product was then distilled at 60° C. and 0.16 mm to give a 68% yield of 4,6-dimethyl-7-acetoxynonan-3-one (8.4 g, 36.8 mmoles).

EXAMPLE 10

Synthesis of 4,6-Dimethyl-7-hydroxynonan-3-one (Compound IVb, FIG. 2) from the acetate A solution of 4,6-dimethyl-7-acetoxynonan-3-one (VI, 4.0 g, 17.5 mmoles) in degassed absolute ethanol was set stirring under a nitrogen atmosphere. After cooling the solution to 10° C., potassium hydroxide (7.5 g, 116 mmoles) in water (7.5 ml) and absolute ethanol (40 ml) was added dropwise over 10 minutes. The yellow solution was then stirred for 18 hours at room temperature.

The procedures for the purification of the pheromone as described by Examples 9 and 10 has not been previously discussed in the literature. However, the methods used in both Examples 9 and 10 are individually well known.

Thus, for example, the acylation of ($\pm$)-serricornin as well as serricornin and isomers has been carried out by many researchers in their pheromone studies. The acylation of an alcohol with acetic anhydride and pyridine is a well established procedure in the art. However, please note that the instant process purifies ($\pm$)-serricornin acetate (VI, FIG. 2) by vacuum distillation. This has not been reported in the literature.

Similarly, the cleavage of an acetate with a base to the corresponding alcohol is a well known chemical reaction. Numerous workers have used this general method for the hydrolysis of ($\pm$)-serricornin acetate and acetate of serricornin isomers to the corresponding alcohol.

It is important to reiterate that no one has reported the purification of ($\pm$)-serricornin by its conversion to the acetate, distillation of the acetate and subsequent base hydrolysis, as well as the base equilibration thereof.

EXAMPLE 11

Equilibration of 4,6-Dimethyl-7-hydroxynonan-3-one, ($\pm$)-serricornin (Compound IVb, FIG. 2)

The equilibration of ($\pm$)-serricornin (IVb) was carried out on a 3.25 g (17.5 mmoles) scale as described in Example 8. A 97% recovery of equilibrated ($\pm$)-serricornin (IVd, 3.15 g, 16.9 mmoles) was observed.

FIELD TRIALS

EXAMPLE 12

Figure 9:
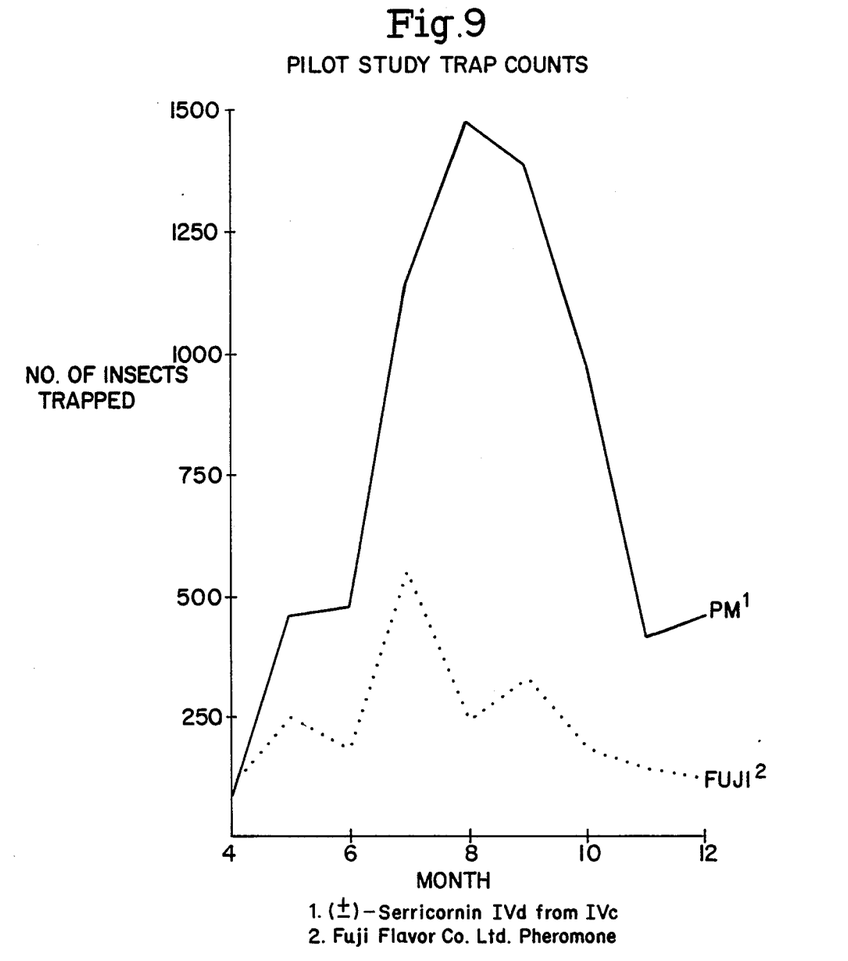
FIGS. 9 and 10 depict results of cigarette beetle trapping tests.
Figure 10:
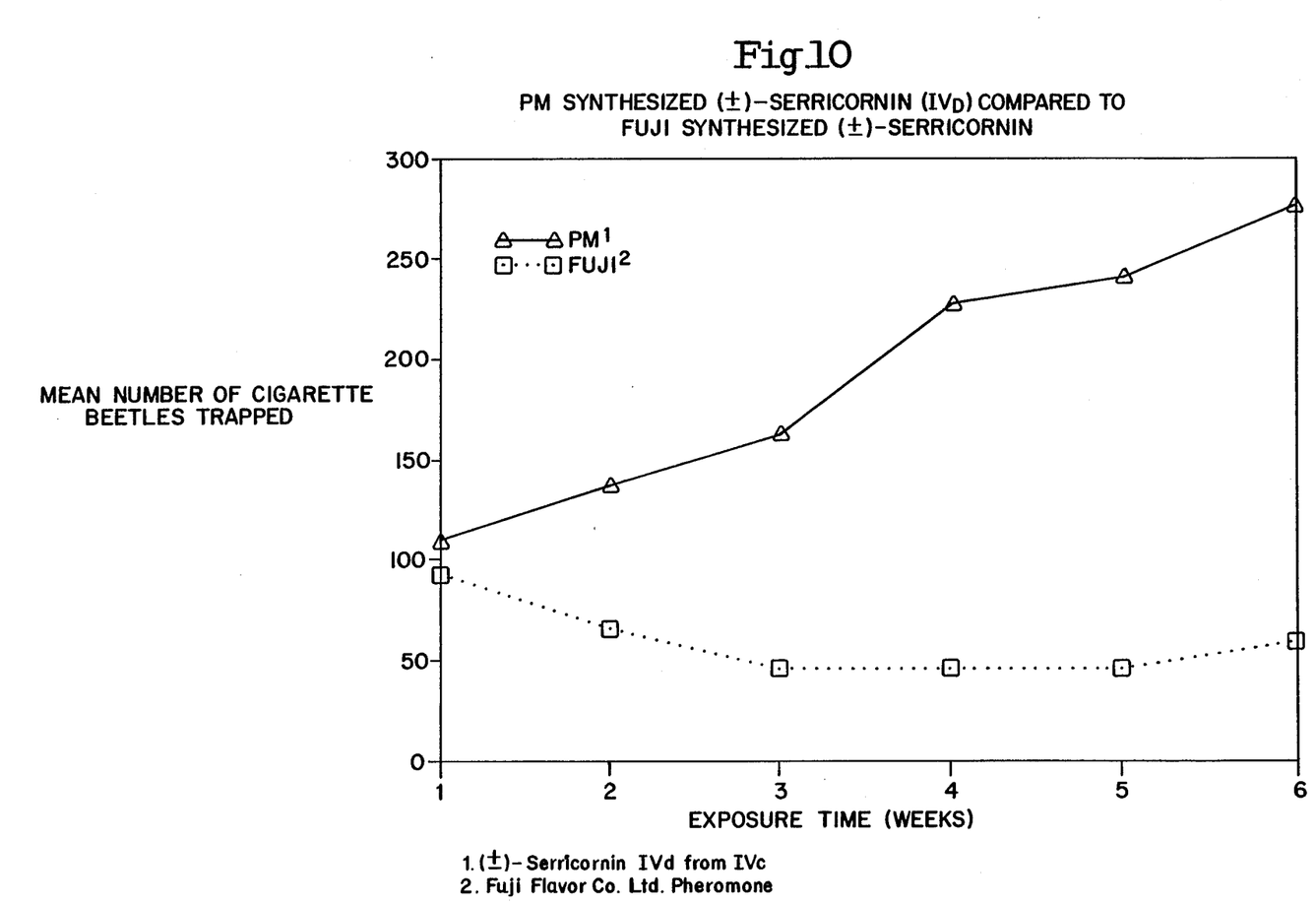

Extensive entymological field testing has been carried out to determine the effectiveness of the ($\pm$)-serricornin, i.e., Compound IVd, FIG. 2, Scheme A as a monitoring tool for attracting the male cigarette beetle. This was accomplished by comparing said Compound IVd against a commercial trap sold under the Trademark ®, by the Fuji Flavor Co., Ltd., as well as against the standard electrical traps already in use in the Phillip Morris facilities. The results of these tests are given in Tables 3 and 4 and illustrated in FIGS. 9 and 10.

The Fuji Serrico ® sex pheromone adhesive trap manufactured by the Fuji Flavor Co., Ltd., Tokyo, Japan, a commercially available product, was the trap system used to compare the instantly synthesized materials with the prior art.

The trap consists of a two-sided folding cardboard body (80 mm × 150 mm × 60 mm) that contains two adhesive strips on the inner surface and slits along the sides for the male beetle to enter. Once the adult male cigarette beetle is lured, the adhesive surface immobilizes the insect.

The Serrico ® kit employs a 1.5 cm absorbent assay disk which contains the serricornin. The absorbent assay disk serves as the controlled release delivery device. Prior to use the assay disk is sealed with a blister package to maintain freshness. Once the disk is removed from the blister package, it is then activated and affixed directly to the adhesive surface of the trap.

In order to test the material of the instant invention, as well as making other comparative tests, a weighted amount usually 50 mg) brought to 100 $\mu$L in pesticide grade hexane of the various pheromones was injected into a cigarette tow, manufactured by the Hoechst Celanese Corporation, which is encapsulated by an extruded plastic cover. The plastic tow measures 9 mm in diameter by 20 mm in length. Even though the target insect attractant is incorporated over and into the entire surface volume (1271.6 mm$^3$) of the Hoechst Celanese tow, the surface area which releases the attractant is confined to the ends (2 × 63.5 square mm). Thus, this design restricts or controls the release rate. Following injection onto the plastic tow, it is affixed to the adhesive surface of the Serrico ® trap.

In testing Compound IVd, made through Scheme A of FIG. 2, 50 mg was used for the majority of the test period. In approximately the last seven weeks of the test, the application rate was 25 mg per tow. A slight drop-off in trapping efficiency was noticed as compared to the 50 mg per tow.

The number of the traps used in the study were as follows:

1. 200 electric grid traps constructed on an aluminum steel frame and anodized aluminum exterior case, 135 cm × 60 cm × 43 cm with a nickel-chrome plated guard and 20 80 watt UV insect attractant lamps (Gilbert, Jonesboro, Arkansas).

2. 100 Serrico ® traps containing the instant synthesized ($\pm$)-serricornin.

3. 100 Serrico ® traps containing the Japanese synthesized ($\pm$)-serricornin.

The electric grid traps had been permanently placed within the manufacturing environment at an earlier time. The pheromone traps were strategically secured on vertical posts, walls, processing machinery, etc. and were alternated every 6 weeks within the monitoring area, thereby removing the possibility of the position to affect either the Fuji or the instantly synthesized pheromones. The number of cigarette beetles trapped was determined on a weekly basis, and fresh lures both for the instantly synthesized pheromones and the Japanese synthesized serricornin were applied every 6 weeks.

The testing results from April to December are shown in detail in Table 3 and are summarized in Table 4. Out of 9,057 cigarette beetles caught on the traps (greater than 99% male), 6,922 or 76% were caught on the traps containing ($\pm$)-serricornin manufactured by the instant process.

TABLE 3

| | Entomological Field Trial April 23–December 26 | | | | | | |
|---|---|---|---|---|---|---|---|
| | 4/23 | 4/30 | 5/7 | 5/14 | 5/21 | 5/29 | Total |
| PM[1] | 23 | 46 | 108 | 116 | 107 | 132 | 532 |

TABLE 3-continued

Entomological Field Trial
April 23–December 26

| | | | | | | | |
|---|---|---|---|---|---|---|---|
| Fuji[2] | 54 | 48 | 40 | 58 | 61 | 93 | 354 |
| Electric Grid | — | — | — | — | — | — | 343 |
| Total | 77 | 94 | 148 | 174 | 168 | 225 | |
| | 6/4 | 6/11 | 6/18 | 6/25 | 7/1 | 7/8 | |
| PM | 88 | 129 | 93 | 170 | 281 | 277 | 1038 |
| Fuji | 88 | 57 | 22 | 17 | 69 | 115 | 368 |
| Electric Grid | — | — | — | — | — | — | 789 |
| Total | 176 | 186 | 115 | 187 | 350 | 392 | |
| | 7/16 | 7/23 | 7/30 | 8/6 | 8/13 | 8/20 | |
| PM | 228 | 145 | 220 | 396 | 432 | 521 | 1942 |
| Fuji | 212 | 98 | 60 | 58 | 50 | 62 | 540 |
| Electric Grid | — | — | — | — | — | — | 1035 |
| Total | 440 | 243 | 280 | 454 | 482 | 583 | |
| | 8/27 | 9/4 | 9/10 | 9/17 | 9/24 | 10/2 | |
| PM | 134 | 328 | 267 | 397 | 399 | 401 | 1926 |
| Fuji | 75 | 122 | 68 | 88 | 57 | 28 | 438 |
| Electric Grid | — | — | — | — | — | — | 787 |
| Total | 209 | 450 | 335 | 485 | 456 | 429 | |
| | 10/8 | 10/15 | 10/22 | 10/29 | 11/5 | 11/12 | |
| PM | 100 | 128 | 188 | 177 | 124 | 161 | 878 |
| Fuji | 48 | 42 | 53 | 17 | 23 | 14 | 197 |
| Electric Grid | — | — | — | — | — | — | 206 |
| Total | 148 | 170 | 241 | 194 | 147 | 175 | |
| | 11/19 | 11/26 | 12/3 | 12/10 | 12/17 | 12/26 | |
| PM | 88 | 49 | 95 | 114 | 95 | 165 | 606 |
| Fuji | 80 | 31 | 33 | 37 | 14 | 43 | 238 |
| Electric Grid | — | — | — | — | — | — | 241 |
| Total | 168 | 80 | 128 | 151 | 109 | 208 | |

[1]($\pm$)-Serricornin IVd from IVc
[2]Fuji Flavor Co. Ltd. pheromone

TABLE 4

Summary of Trapping Efficiencies[1]

| Trap Type | No. of Traps | No of Cigarette Beetles Trapped | Gender Trapped |
|---|---|---|---|
| Electric Grid | 200 | 3401 | Male & Female |
| PM Pheromone-IVd | 100 | 6922 | Male |
| Fuji Pheromone-"Serrico" ® | 100 | 2135 | Male |

[1]Summary of data from Table 3

EXAMPLE 13

Another field test was conducted at a tobacco warehouse for a period of 11 days. All the material synthesized in accordance with the process of this invention, either purified, partially purified, or fully purified, were loaded onto the standard traps previously described at 70 mg per tow. The commercially available Serrico ® trapping system from Fuji Flavor Company was employed, excluding the food attractant disk. The control was the Serrico ® trap minus the pheromone and food attractant disks, the traps were rotated, and the counts were taken every 2 to 3 days. The results are shown in Table 5.

TABLE 5

The Actual Number of Cigarette Beetles Trapped by Each Treatment in a Tobacco Warehouse Within 2 and 3 Day Intervals

| September 3 | 6 | 9 | 12 | 14 | Treatment Total | % Trapped |
|---|---|---|---|---|---|---|
| CONTROL | 69 | 25 | 34 | 19 | 147 | 2.7 |
| ($\pm$)-Anhydro-serricornin (V) | 16 | 13 | 10 | 9 | 48 | .9 |
| 25:75[a] | 70 | 62 | 89 | 50 | 271 | 5.0 |
| 50:50[a] | 73 | 65 | 150 | 65 | 353 | 6.5 |
| 75:25[a] | 86 | 95 | 122 | 64 | 367 | 6.8 |
| ($\pm$)-Serricornin (IVa) | 86 | 68 | 189 | 93 | 436 | 8.1 |
| ($\pm$)-Serricornin (IVd) | 731 | 402 | 922 | 923 | 2978 | 55.1 |
| "Serrico" ® | — | 203 | 356 | 247 | 806 | 14.9 |
| WAREHOUSE TOTAL | 1131 | 933 | 1872 | 1470 | 5406 | 100.0 |

[a]($\pm$)-Serricornin (IVa):($\pm$)-Anhydroserricornin (V)

The above results clearly demonstrate the improved activity of the ($\pm$)-serricornin made in accordance with the novel process of this invention. Thus, for example, Table 5 shows the results obtained with ($\pm$)-anhydroserricornin (V) as well as mixtures of the unpurified ($\pm$)-serricornin (IVa from FIG. 1) in admixture with various amounts of anhydroserricornin (V). Table 5 also clearly shows the results obtained with the unpurified serricornin, i.e., Compound IVa of FIG. 1, as well as the fully purified ($\pm$)-serricornin of this invention, i.e., Compound IVd from FIG. 2, Scheme A. As can be seen, the fully purified material was vastly superior in its ability to trap cigarette beetles.

EXAMPLE 14

This Example will illustrate that ($\pm$)-serricornin purified by scheme B of FIG. 2 is effective.

Equilibrated ($\pm$)-serricornin (IVd) synthesized from the acetate intermediate (VI) was tested in a manufacturing facility at Philip Morris.

Twenty traps containing ($\pm$)-serricornin (IVd from VI) were prepared as previously described at a load level of 70 mg per trap. An additional 20 traps at a load level of 70 mg per trap were prepared using equilibrated ($\pm$)-serricornin (IVd) synthesized via the anhydroserricornin (V).

Table 6 summarizes the results over a four week testing period. From all indications, the equilibrated ($\pm$)-serricornin prepared from the acetate intermediate appears to be as successful as equilibrated ($\pm$)-serricornin prepared through the anhydroserricornin intermediate.

TABLE 6

| Week No. | Procedure B FIG. 2 20 Traps of IVd from VI | Procedure A FIG. 2 20 Traps of IVd from V |
|---|---|---|
| 1 | 10 | 10 |
| 2 | 3 | 4 |
| 3 | 19 | 10 |
| 4 | 20 | 5 |

The following Examples 15 and 16 will demonstrate that the novel process of this invention is crucial in producing a ($\pm$)-serricornin of enhanced activity. If conventionally available serricornins are purified by the exact same procedure, i.e., Scheme A of FIG. 2, equivalent results will not be obtained since the ($\pm$)-serricornin has not gone through all steps of the process. Additionally, these experiments will demonstrate that if one were to purify the (±)-serricornin produced by the instant process up to IVa of FIG. 1 by conventional distillation as opposed to carrying out the remaining steps shown in FIG. 2, inferior results will have been obtained.

EXAMPLE 15

This example will again demonstrate that the total process for the preparation of the (±)-serricornin is necessary in order to obtain a material of enhanced activity. This experiment compares Compound IVd purified via method A of FIG. 2 with Compound IVa of FIG. 1 which purified by conventional distillation.

The experimental traps utilized have been previously described and the following Table 7 represents the data obtained over a 6-week monitoring period.

TABLE 7

| Monitoring Period (Weeks) | Sample Preparations | | | | IVd (total) | IVa (total) |
|---|---|---|---|---|---|---|
| | Experiment #1 | | Experiment #2 | | | |
| | IVd | IVa | IVa | IVa | | |
| 1 | 159 | 7 | 40 | 3 | 199 | 10 |
| 2 | 160 | 3 | 118 | 6 | 278 | 9 |
| 3 | 99 | 1 | 143 | 4 | 242 | 5 |
| 4 | 117 | 6 | 150 | 18 | 267 | 24 |
| 5 | 66 | 1 | 41 | 0 | 107 | 1 |
| 6 | 11 | 1 | 26 | 0 | 37 | 1 |
| | 612 | 19 | 518 | 31 | 1130 | 50 |

As can be seen from the above table, this experiment was run in duplicate and consistently Compound IVd which was prepared according to FIG. 2, procedure A, was far superior in activity to Compound IVa which is the material of FIG. 1 purified by conventional distillation. The above table clearly demonstrates the fact that (±)-serricornin cannot merely be distilled in order to obtain enhanced activity, i.e., see the results with Compound IVa, but the entire purification process, as well as the synthesis process, must be utilized in order to obtain superior results.

EXAMPLE 16

The following examples will again illustrate that merely carrying out the purification procedure, as set forth in FIG. 2, on any (±)-serricornin does not result in the improved results of the instant process. In these examples which were run in duplicate, a sample of a commercial pheromone provided by the British American Tobacco Company for its Lasiotrap ® cigarette beetle was tested in the manner previously described.

As received, this material is labelled A. A sample of A was purified via route A of FIG. 2 and this material is labelled B.

Both of the materials were evaluated for cigarette beetle attraction over a 6-week monitoring period with the following results.

TABLE 8

| Monitoring Period (Weeks) | Sample Preparations | | | | A (total) | B (total) |
|---|---|---|---|---|---|---|
| | Experiment #3 | | Experiment #4 | | | |
| | A | B | A | B | | |
| 1 | 349 | 97 | 121 | 3 | 470 | 100 |
| 2 | 244 | 49 | 218 | 36 | 462 | 85 |
| 3 | 81 | 50 | 112 | 46 | 193 | 96 |
| 4 | 100 | 41 | 140 | 6 | 240 | 47 |
| 5 | 84 | 9 | 300 | 26 | 384 | 35 |
| 6 | 3 | 0 | 14 | 3 | 17 | 3 |
| | 861 | 246 | 892 | 120 | 1766* | 366* |

*Significantly different (at the 0.05 confidence level) based on statistical analysis of variance and covariance with repeated measures (J. Tindall).
British American Tobacco (BAT) Lasiotrap ® pheromone unmodified
British American Tobacco (BAT) Lasiotrap ® pheromone purified via step V as per the invention record Scheme I.
(#) Alternate warehouse that traps were moved to for duration of the study (last 2 weeks) since original warehouse were being fumigated.

As can be seen from the two experiments above, the pheromone purified via procedure A of FIG. 2 actually gave poorer performance with regard to the number of adult cigarette beetles trapped than did the unmodified material. Thus, the mere application of the purification technique of FIG. 2 to any pheromone does not result in enhanced activity.

EXAMPLE 17

The following example will demonstrate how Compound IVa of FIG. 1 was distilled in the tests above reported in Example 15.

Compound IVa (10.0 g, 0.5 moles) was distilled on a short path distillation apparatus (short path distillation head) with attached Vigreaux distillation column (30 mm). The distillation at 50–72° C. and 0.080 mm gave a 43.3% yield of distilled IVa (4.33 g, 0.023 mole).

TABLE 9

| Temp (°C.) | | Vacuum (mm of Hg) | Result |
|---|---|---|---|
| Pot | Head | | |
| R.T. | R.T. | 0.20–0.080 | Nothing collected |
| R.T.–100 | R.T.–50 | 0.080 | Start of distillation |
| 100–120 | 50–72 | 0.080 | 4.33 g distilled IVa |
| 120–150 | 72–45 | 0.080 | Nothing collected |

| GLOSSARY | |
|---|---|
| Serricornin: | (4S, 6S, 7S)-4,6-Dimethyl-7-hydroxy-3-nonanone The terms Serricornin and (±)-Serricornin have been used throughout this application to refer to both open and hemiacetal (closed) forms: |
| (±)-Serricornin: | 4,6-Dimethyl-7-hydroxy-3-nonanone (NOTE: See above) |
| Enantiomeric pair: | Stereoisomers which are related as object and nonsuperimposable mirror image. |
| Enantiomer: | One of enantiomeric pair |
| Optical isomer: | An enantiomer |
| Diasteriomer: | Stereoisomer which is not an enantiomer |
| Isomers: | Chemical species which have the same molecular formula but differ in structure and are separated by energy barriers. |
| Constitution of a molecule: | The description of the sequential arrangement of atoms regardless of the direction in space. |
| Chiral Carbon or Asymmetric Carbon Atom: | A carbon to which four substituents are attached which differ in the sense that exchange of any two gives a new stereoisomer |

| -continued | |
|---|---|
| GLOSSARY | |
| Anhydroserricornin: | (5S,6S)-2,6-Diethyl-5,6-dihydro-3,5-dimethyl-2H-pyran [NOTE: This term also used in the literature to refer to the racemic anhydroserricornin (See (±)-anyhdroserricornin)] |
| Racemic Compound: | An equal mixture of enantiomers |
| (±)-Anhydroserricornin: | 2,6-Diethyl-5,6-dihydro-3,5-dimethyl-2H-pyran |
| R* or S*: | Designates racemic carbon and equivalent of mixture of 1:1 R and S. |
| Stereoisomers: | Molecules with the same constitution but differing, as isomers, in the spatial arrangement of these atoms. |
| Threo Isomers: | Stereoisomer with the substituents on the opposite sides of the Fischer projection |
| Erythro Isomer: | Stereoisomer with the substituents on the same side of the Fischer projection. |
| Threo Isomers of Serricornin: | The 6,7-threo diasteriomers which are compounds IV.1-IV.4. |
| Erythro Isomers of Serricornin: | The 6,7-erythro diastereomers which are compounds IV.5-IV.8. |

What is claimed:

1. In a process for the preparation of (±)-serricornin wherein 2,4-dimethyl-5-oxoheptanenitrile is converted to crude (±)-serricornin via a Grignard reaction the improvement which comprises
   (1) subjecting said 2,4-dimethyl-5-oxoheptanenitrile to a base equilibration step by treatment of the same in an organic solvent in the presence of a base for a period of time sufficient to produce the thermodynamic diastereomer ratio dissolved in said organic solvent;
   (2) reducing said dissolved 2,4-dimethyl-5-oxoheptanenitrile from step (1) to 2,4-dimethyl-5-hydroxyheptanenitrile with sodium borohydride in the presence of added base;
   (3) subjecting said 2-4-dimethyl-5-hydroxyheptanenitrile from step (2) to a Grignard reaction to convert the same to crude (±)-serricornin;
   (4) subjecting said crude (±)-serricornin to either of the following procedures
      (a) treating said crude (±)-serricornin, dissolved in an organic solvent with an acid catalyst in order to produce an anhydroserricornin and then subjecting said anhydroserricornin to treatment with perchloric acid and dioxane in order to obtain purified (±)-serricornin; or
      (b) forming the acetate from said crude (±)-serricornin followed by distillation and hydrolysis of the same to purified (±)-serricornin;
   (5) treating said purified (±)-serricornin from either A or B to a base equilibration step in order to obtain pure equilibrated (±)-serricornin.

2. The process of claim 1 wherein the base equilibration of Step 1 is carried out at room temperature.

3. The process of claim 2 wherein the base is an alkali or alkaline earth metal hydroxide.

4. The process of claim 3 wherein said base is sodium hydroxide.

* * * * *